US008876825B2

(12) United States Patent
Victor

(10) Patent No.: US 8,876,825 B2
(45) Date of Patent: Nov. 4, 2014

(54) DISPOSABLE CYLINDRICAL CUTTER

(75) Inventor: Gary C. Victor, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 109 days.

(21) Appl. No.: 13/112,084

(22) Filed: May 20, 2011

(65) Prior Publication Data

US 2011/0288554 A1    Nov. 24, 2011

Related U.S. Application Data

(60) Provisional application No. 61/346,976, filed on May 21, 2010.

(51) Int. Cl.
*A61B 17/16* (2006.01)
*A61B 17/17* (2006.01)

(52) U.S. Cl.
CPC ........... *A61B 17/1668* (2013.01); *A61B 17/175* (2013.01); *A61B 17/162* (2013.01); *A61B 17/1659* (2013.01); *A61B 17/1637* (2013.01)
USPC .................................. 606/79; 606/80; 606/84

(58) Field of Classification Search
USPC ............... 606/79–86 R, 89, 167–189; 30/276
See application file for complete search history.

(56) References Cited

U.S. PATENT DOCUMENTS

| | | | | |
|---|---|---|---|---|
| 1,569,987 A * | 1/1926 | Lamberti | ........................ | 30/276 |
| 2,832,184 A * | 4/1958 | Beuerle | .......................... | 56/17.2 |
| 3,118,162 A * | 1/1964 | Karr et al. | ........................ | 15/180 |
| 3,398,422 A * | 8/1968 | Barry et al. | ..................... | 15/180 |
| 3,877,146 A * | 4/1975 | Pittinger | ........................ | 30/276 |
| 4,148,110 A * | 4/1979 | Moen | .............................. | 15/385 |
| 4,211,002 A * | 7/1980 | Kirk | ............................. | 30/123.3 |
| 4,284,080 A * | 8/1981 | Rehder | ........................... | 606/80 |
| 4,306,550 A * | 12/1981 | Forte | .............................. | 606/85 |
| 4,335,510 A * | 6/1982 | Close et al. | ..................... | 30/276 |
| 4,547,966 A * | 10/1985 | Eden | .............................. | 30/300 |
| 5,100,267 A | 3/1992 | Salyer | | |
| 5,180,384 A * | 1/1993 | Mikhail | ........................ | 606/80 |
| 5,205,685 A * | 4/1993 | Herbert | ........................ | 408/204 |
| 5,282,804 A * | 2/1994 | Salyer | ......................... | 606/86 R |
| 5,295,992 A * | 3/1994 | Cameron | ........................ | 606/79 |
| 5,299,893 A * | 4/1994 | Salyer et al. | .................... | 407/54 |
| 5,336,226 A * | 8/1994 | McDaniel et al. | .............. | 606/79 |
| 5,493,783 A * | 2/1996 | Oostendorp | .................... | 30/276 |
| 5,501,686 A * | 3/1996 | Salyer | ............................. | 606/79 |
| 5,876,405 A * | 3/1999 | Del Rio et al. | .................. | 606/80 |

(Continued)

FOREIGN PATENT DOCUMENTS

| | | |
|---|---|---|
| DE | 20115678 | 12/2001 |
| EP | 0574701 A1 | 5/1993 |
| WO | 2008001104 | 1/2008 |

OTHER PUBLICATIONS

European Search Report dated Apr. 18, 2013, EP11167163.

*Primary Examiner* — Matthew Lawson
*Assistant Examiner* — Zade Coley
(74) *Attorney, Agent, or Firm* — Michael F. Scalise

(57) ABSTRACT

A single use bone cutter comprised of two concentric cylinders and a series of insert blades or cutter disc is described. The cutter blades or cutter disc is preferably positioned at the distal end of the cutter. The bone cutter also comprises a guide rod that aids in the line of sight when using the cutter device.

18 Claims, 10 Drawing Sheets

(56) References Cited

U.S. PATENT DOCUMENTS

| | | | |
|---|---|---|---|
| 5,976,143 A * | 11/1999 | McCue | 606/80 |
| 6,162,227 A | 12/2000 | Eckhardt | |
| 6,277,121 B1 * | 8/2001 | Burkinshaw et al. | 606/80 |
| 6,322,564 B1 * | 11/2001 | Surma | 606/79 |
| 6,588,111 B2 * | 7/2003 | Williams | 30/391 |
| 7,527,696 B1 * | 5/2009 | Aus | 134/6 |
| 8,057,477 B2 * | 11/2011 | Desarzens et al. | 606/80 |
| 8,152,809 B1 * | 4/2012 | Kao et al. | 606/80 |
| 2003/0135219 A1 * | 7/2003 | Salyer et al. | 606/81 |
| 2003/0212401 A1 * | 11/2003 | Nordman | 606/80 |
| 2005/0039583 A1 * | 2/2005 | McNulty | 83/13 |
| 2005/0251145 A1 * | 11/2005 | Desarzens et al. | 606/80 |
| 2006/0111725 A1 | 5/2006 | Biegun | |
| 2009/0118735 A1 * | 5/2009 | Burmeister et al. | 606/80 |
| 2009/0209963 A1 * | 8/2009 | Jamali | 606/81 |
| 2009/0326536 A1 | 12/2009 | Pynsent | |
| 2010/0004653 A1 * | 1/2010 | Rasekhi | 606/85 |
| 2010/0152742 A1 * | 6/2010 | Nevelos et al. | 606/89 |

\* cited by examiner

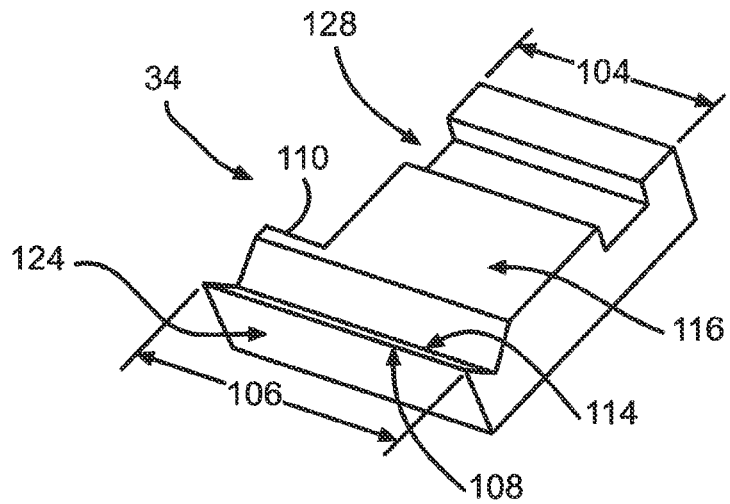
FIG. 5
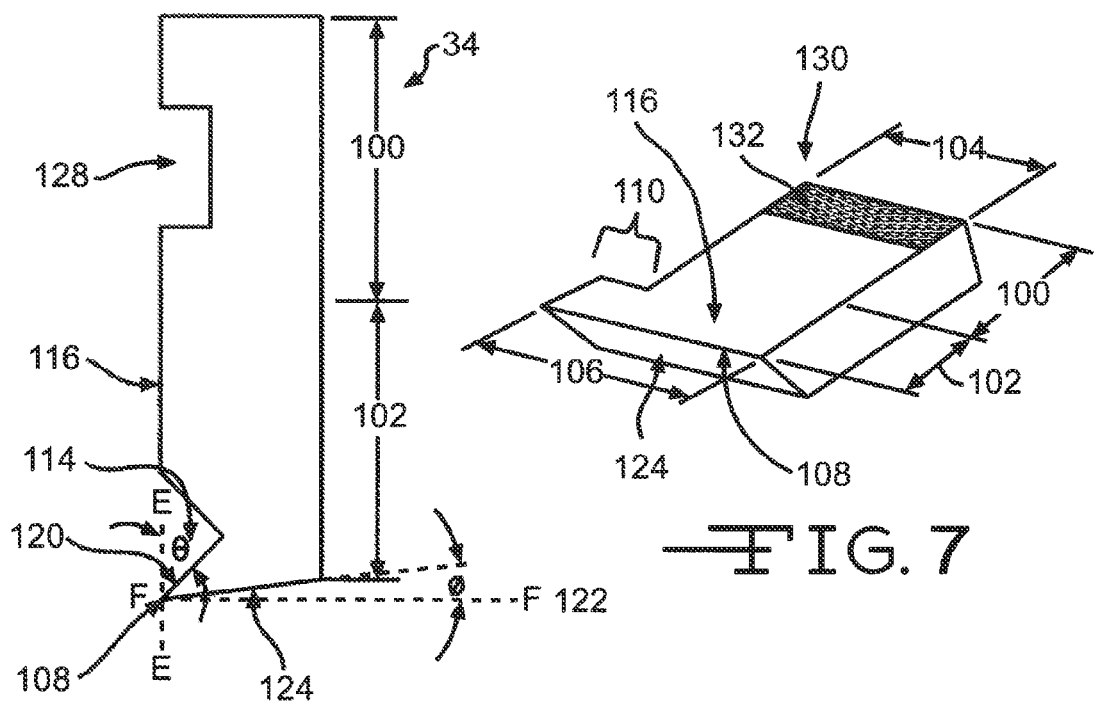
FIG. 6
FIG. 7

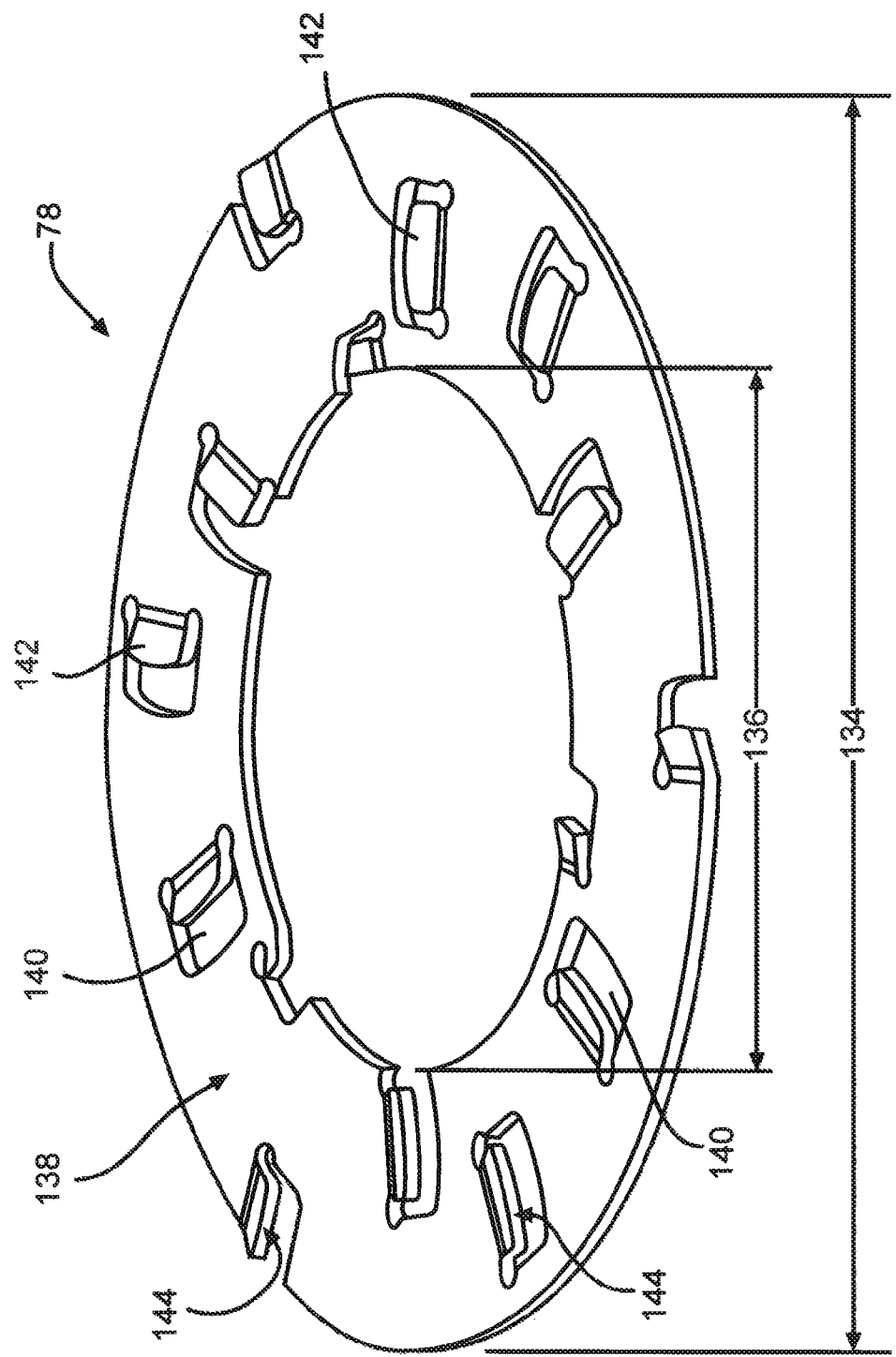

DISPOSABLE CYLINDRICAL CUTTER

CROSS-REFERENCE TO RELATED APPLICATIONS

This application claims priority from U.S. Provisional Patent Application Ser. No. 61/346,976, filed May 21, 2010.

FIELD OF THE INVENTION

The present invention relates to the art of orthopedic cutting tools, and more particularly, to a disposable cutter used for shaping and preparing the femoral bone for implant insertion.

PRIOR ART

Cutting tools used in orthopedic procedures are designed to cut bone and associated tissue matter. Specifically, cutters of the present invention are designed to cut and shape the end of a long bone such as a femur or humerus. Typically, the end of the long bone is cut and shaped for insertion of an implant. As such, these cutters are required to be sterile and sharp. Using a dull cutter generates heat that typically leads to tissue necrosis and results in undesireable patient outcomes. A non-sterile cutter blade typically results in an infected and damaged bone that may lead to other problems for the patient.

Depicted in FIGS. 1 and 1A are images of a prior art bone cutter 10 designed to cut and shape the femoral head 12 of the femur 14. As shown in the figures, the prior art cutter 10 is similar to that of a "hole saw" drill. These prior devices 10 generally comprise a hollow cylinder in which a series of cutting teeth slots 16 are formed within the cylinder wall thickness 18. However, these prior devices 10 do not remove all the bone 14 required to properly fit an implant. Therefore, additional procedures are required to remove this extra bone material 22 and smooth the surface of the bone end 24.

As shown in FIG. 1A, the prior cutter device 10 imparts a channel 20 within the end 24 of the bone 14. This channel 20 and associated bone material 22 proximate the channel 20, must be removed to properly fit the implant (not shown) on the end 24 of the bone 14. Typically, hand tools such as rongeurs are used to remove this extra bone material 22.

Such a bone removal procedure makes it difficult to properly fit an implant over the end 24 of the bone 14. The extra bone material 22 must be intricately removed to produce a smooth surface and ensure that the bone 14 is shaped to meet the exacting dimensions of the implant. If the implant is not properly fit over the end 24 of the bone 14, undesirable implant wear or improper implant operation could result.

In addition to the inefficient bone removal limitations, traditional bone cutters are typically reused multiple times. That is because of their high cost. Such multiple reuses require that the cutter be cleaned and sterilized before each use. Furthermore, over time, as these cutters are used and reused, they become dull, thus requiring resharpening. Therefore the blades of the cutter are required to be resharpened, cleaned and sterilized. However, these resharpening and sterilization processes add additional costs and increase the possibility of infection. In addition, resharpening tends to deform the dimensions of the cutter. These dimensional changes could adversly impact the optimal fit and function of the implant. Furthermore, there is a high likelihood that the cleaning and sterilization process may not remove all possible infection agents such as bacteria, machining lubricants, and the like.

Accordingly, the present invention provides a cost effective single use bone cutter with a novel blade and assembly design that improves cutting efficiency. The enhanced bone cutting and shaping efficiencies of the present invention ensure proper implant fit and reduced implant wear. In addition, the improved bone cutting efficiencies afforded by the present invention, decrease procedural time and minimize patient trauma. Furthermore, the bone cutter of the present invention ensures proper cutter sharpness and cleanliness that promotes optimal patient outcomes.

SUMMARY OF THE INVENTION

The present invention provides a disposable bone cutter device comprising a cutter assembly and guide rod for orthopedic surgical applications. Specifically, the cutter device of the present invention is designed to re-shape the head of a femur for joint revision surgeries.

The cutter assembly comprises a disposable housing and a series of insert blades or a cutter disc arranged in circumferential manner within the assembly. The series of insert blades or cutter disc are preferably secured in the cutter assembly through an interference fit at a distal base portion of the cutter assembly.

The housing comprises two cylinders that are joined together at a distal portion of the housing. In a preferred embodiment, a first cylinder is positioned such that its inner diameter circumferentially surrounds the outer diameter of a second cylinder. Both the first and second cylinders are positioned such that they share a common central longitudinal axis. A series of radial connectors join the two cylinders together along the distal base portion of the assembly. In a preferred embodiment, these connectors may take the form of a bar or rod or alternatively be formed into a blade enclosure designed to secure and house the individual insert cutter blades.

Furthermore, it is preferred that the distal base portion of the centrally located second cylinder is recessed or offset from the distal base of the first cylinder. This recess establishes an offset rim formed by the wall thickness of the first cylinder. The depth of the offset rim is determined by the gap between the distal base plane of the first cylilnder and the distal base plane of the second cylinder. The offset rim provides a barrier that prevents unintentional damage to nearby bone and/or tissue resulting from contact with the cutting surface of the insert blades or cutting disc.

Located at the proximal end portion of the assembly, within the interior of the inner diameter of the centrally located second cylinder, is a boss. The boss comprises a central throughbore that is positioned such that the throughbore is coaxial with the common longitudinal axis. The throughbore of the boss provides an alignment aid to the axis of the desired cut.

Another feature of the boss is that it acts as a "stop" to prevent overcutting of the bone. As will be explained in greater detail, the distal end of the boss comes into contact with the end of the bone thus preventing further advancement of the cutter. As such, the position of the boss preferably determines the depth of cut into the bone and prevents unintentional overcutting of the end of the bone.

The boss is joined within the interior of the second cylinder through a series of rods which radially extend between the exterior wall surface of the boss and an interior wall surface of the inner diameter of the second cylinder. In addition, these rods serve as an interfacing feature by which the cylindrical cutter attaches to a handle or a motor that rotates the cutter in a clockwide or counterclockwise direction. In a preferred embodiment, the housing can be produced as a single component using an injection molding process.

The insert blades are universal and can be manufactured to a minimal size to accommodate all sizes of the cutter. In a preferred embodiment, the series of individual cutter blades are secured within their respective blade enclosures. These blades are preferably of an "L" shape and are designed to provide a cutting edge that extends into the interior of the centrally located second cylinder.

The cutter insert blades preferrably include a slot, residing within the surface that extends along the width of the blade. The slot is designed to interface with a post positioned within the blade enclosure. The interaction between the post and slot secures the insert blade therewithin.

In this embodiment, the cylindrical cutter is assembled by pressing the insert blades into the blade enclosures of the assembly. The insert blades are designed such that they snap into the blade enclosure. This low cost production process, along with the economical production of the component parts, avoids the need for expensive machining and grinding operations that are common with the prior art.

In an alternate embodiment, a cutter disc having a plurality of cutting teeth openings, resides within the distal base portion of the assembly. In a preferred embodiment, the cutting disc comprises an outer diameter, an inner diameter, and a planar surface therebetween. The plurality of cutting teeth are positioned at spaced intervals throughout the planar surface.

In operation, the femoral head is first shaped to accept a replacement shell of an implant utilizing the present invention. The shaping of the femoral head is accomplished by first establishing an axis of cut on the femoral head. This axis is established by drilling a guide hole into the femoral head and placing a guide rod into the bone. This guide rod serves to align the axis of the cylindrical cutter to the axis of the intended cut. The cutter of the present invention is then attached to the handle-driver assembly and positioned over the guide rod by means of the hollow boss within the cylindrical cutter. The powered driver provides a means of rotating the cylindrical cutter and advancing the cutter against the femoral head.

BRIEF DESCRIPTION OF THE DRAWINGS

FIG. 5 is a perspective view of an embodiment of a cutter blade of the present invention.

FIG. 6 is a side view of the embodiment of the cutter blade shown in FIG. 5.

FIG. 7 is a perspective view of an alternate embodiment of a cutter blade of the present invention.

FIG. 9 is a perspective view of a preferred embodiment of a cutter disc of the present invention.

DETAILED DESCRIPTION OF THE PREFERRED EMBODIMENTS

Figure 10:
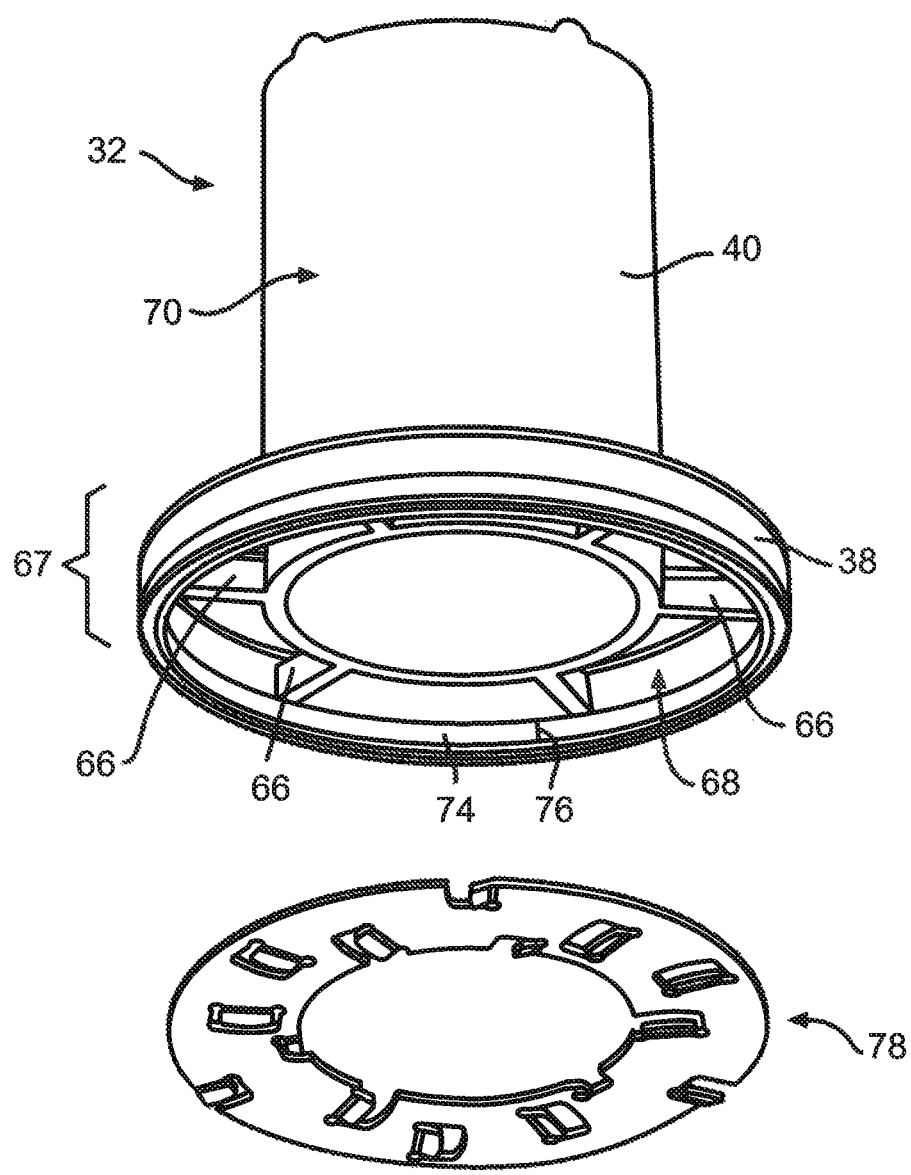
FIG. 10 is a perspective view of the cutter disc and an alternative cutter housing embodiment of the present invention.
Figure 11:
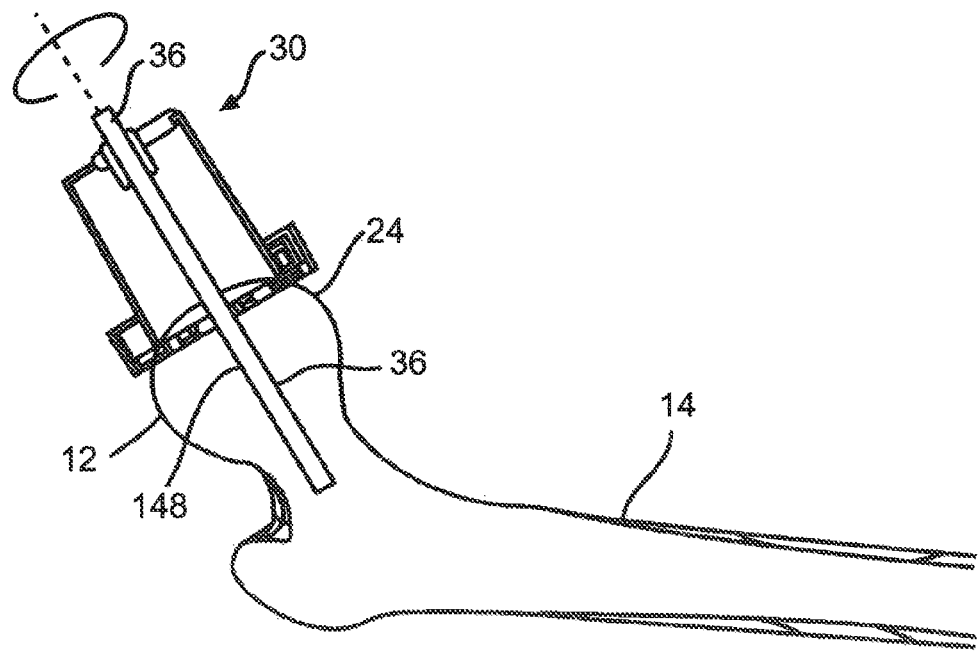
FIG. 11 is a cross-sectional view of an embodiment of the bone cutter of the present invention being used to shape the end of a bone.
Figure 11A:
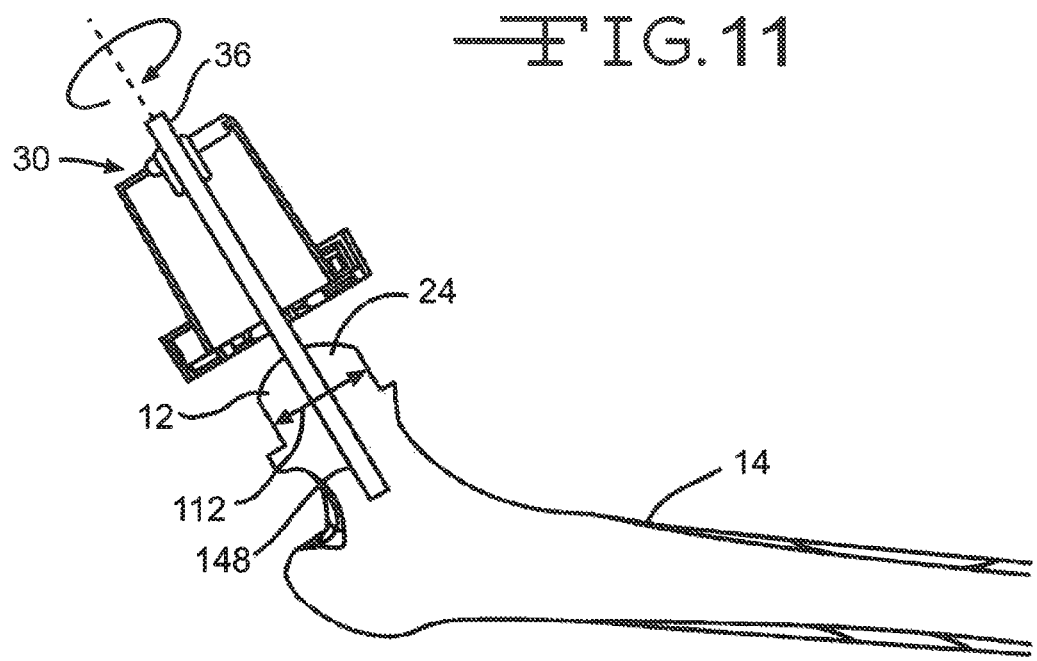
FIG. 11A is a cross-sectional view illustrating the shaped end of a bone after using the bone cutter of the present invention.

Now turning to the figures, FIGS. 2-11A illustrate embodiments of a bone cutter 30 of the present invention. In a preferred embodiment, the bone cutter 30 comprises a cutter housing 32, cutter blades 34 or cutter disc 78, and a guide rod 36 (FIGS. 11, 11A).

As shown in FIGS. 2-4, 8, 8A, and 10-11A, the cutter housing 32 preferably comprises two cylinders, a first cylinder 38 and a second cylinder 40 that are joined therebetween. In a preferred embodiment, the first cylinder 38 comprises a first cylinder inner diameter 42, a first cylinder outer diameter 44, and a first cylinder wall thickness 46 therebetween. The second cylinder 40 comprises a second cylinder inner diameter 48, a second cylinder outer diameter 50, and a second cylinder wall thickness 52 therebetween.

Figure 4:
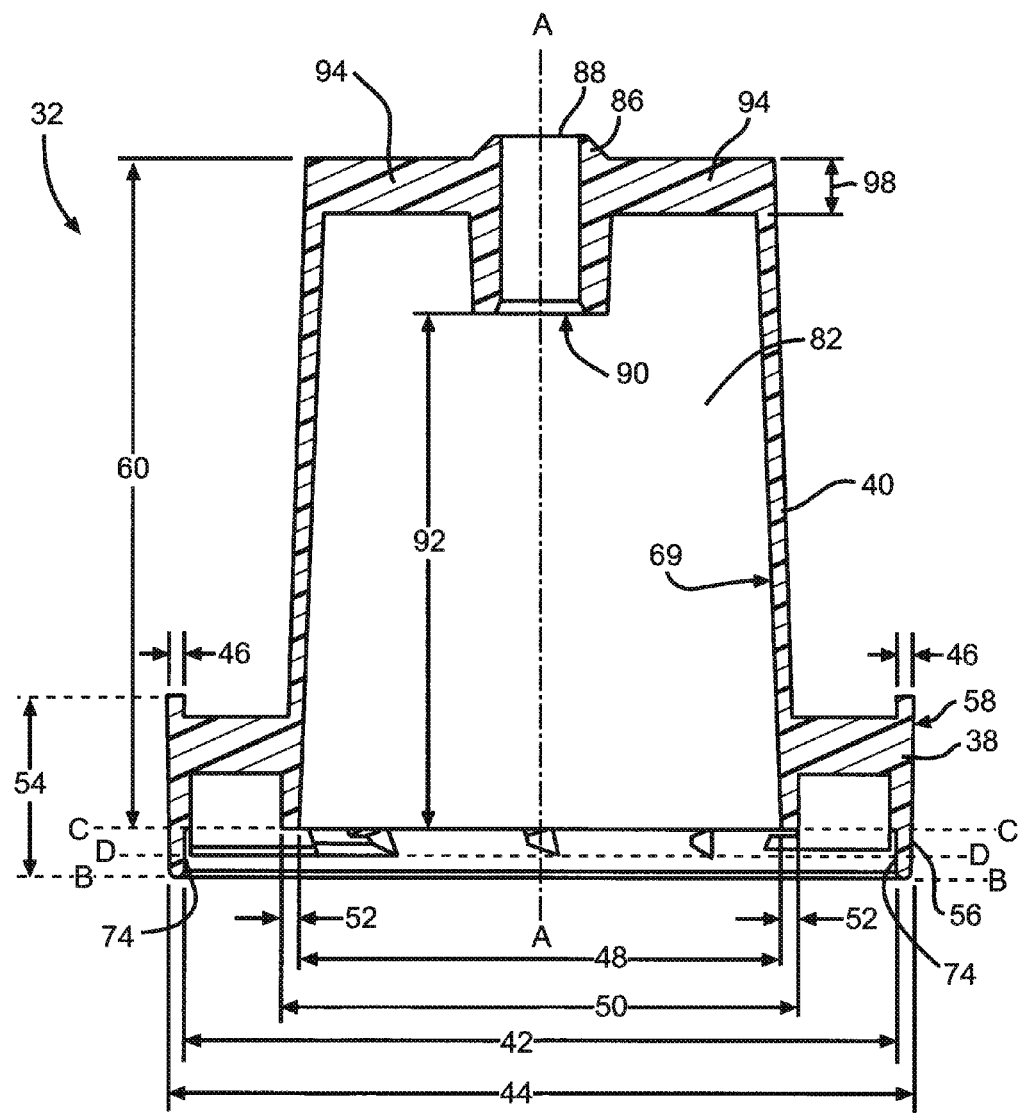
FIG. 4 is a cross-sectional view of the cutter housing of the present invention.

In addition, the first cylinder 38 comprises a first cylinder height 54 extending from a first cylinder distal base portion 56 to a first cylinder proximal end portion 58. In a preferred embodiment, the distal base portion 56 of the first cylinder 38 is co-planar with an imaginary first cylinder base plane B-B (FIG. 4). This imaginary base plane B-B preferably extends outwardly from the outer diameter 44 of the first cylinder base portion 56.

The second cylinder 40 comprises a second cylinder height 60 extending from a second cylinder distal base portion 62 to a second cylinder proximal end portion 64. In a preferred embodiment, the distal base portion. 62 of the second cylinder 40 is co-planar with an imaginary second cylinder base plane C-C (FIG. 4). This imaginary base plane C-C preferably extends outwardly from the outer diameter 50 of the second cylinder base portion 62.

In a preferred embodiment, the first and second cylinders 38, 40 are joined such that the outer diameter 50 of the second cylinder 40 is positioned within the inner diameter 42 of the first cylinder 38. The first and second cylinders 38, 40 are further positioned such that they are co-axial to a common central longitudinal axis A-A as shown in FIGS. 2-4, 8, 8A, and 10-11A.

In a preferred embodiment, the outer diameter 44 of the first cylinder 38 ranges from about 5 cm to about 10 cm, the inner diameter 42 of the first cylinder 38 ranges from about 4.5 cm to about 9.95 cm and the height 54 of the first cylinder 38 ranges from about 1 cm to about 4 cm. The wall thickness 46 of the first cylinder 38 preferably ranges from about 0.05 cm to about 0.5 cm.

In a preferred embodiment, illustrated in FIGS. 2-4, 8, 8A, and 10-11A, the height 60 of the centrally located second cylinder 40 is greater than that of the height 54 of the first cylinder 38. Furthermore, the height 60 of the centrally located second cylinder 40 ranges from about 5 cm to about 10 cm. The outer diameter 50 of the second cylinder 40 ranges from about 3 cm to about 6 cm and the inner diameter 48 of the second cylinder 40 ranges from about 2 cm to about 6 cm. The wall thickness 52 of the second cylinder 40 ranges from about 0.05 cm to about 0.5 cm.

The two cylinders 38, 40 are joined together by a connector 66 that interfaces between the two cylinders 38, 40 at a distal end portion 67 of the housing 32 as shown in FIG. 10. The connector 66 can be of many non-limiting forms such as a bar, a rod, a rectangle or a sphere such that one surface interfaces with the interior wall surface 68 of the inner diameter 42 of the first cylinder 38 and an opposite surface interfaces with the exterior wall surface 70 of the outer diameter 50 of the second cylinder 40. In a preferred embodiment, a plurality of two or more connectors 66, radially extend between the inner and outer diameters 42, 50 of the first and second cylinders 38, 40, respectively, and join them therebetween as shown in FIG. 10.

In a preferred embodiment, the connector 66 can be designed as a blade enclosure 72 such that individual insert blades 34 (FIGS. 2-3, and 8-8A) are disposed therewithin. This preferred blade enclosure 72 embodiment, will be discussed in more detail.

As shown in the embodiments illustrated in FIGS. 3-4, 8-8A, and 10-10A, the housing 32 is preferably constructed such that an offset rim 74 is formed by a portion of the wall thickness 46 of the first cylinder 38. The depth 76 of the offset rim 74 is defined by the distance between the first and second imaginary distal base planes B-B, C-C as shown in the cross sectional view of FIG. 4. In a preferred embodiment, the offset rim 74 preferably has a depth 76 that ranges from about 0.01 cm to about 0.05 cm. The offset rim 74 preferably extends around the perimeter of the first cylinder 38 at the distal base portion 56. The thickness of the offset rim 74 is defined by the wall thickness 46 of the outer first cylinder 38.

The offset rim 74 is designed to prevent the cutter blades 34 or cutter disc 78 (FIG. 9) from inadvertently damaging nearby bone or tissue, particularly preventing a proximal bone or tissue from being cut or nicked. However, it is contemplated that the housing 32 could be constructed such that the first and second imaginary planes B-B, C-C are coplanar, therefore constructing a housing 32 without an offset rim 74.

Figure 8:
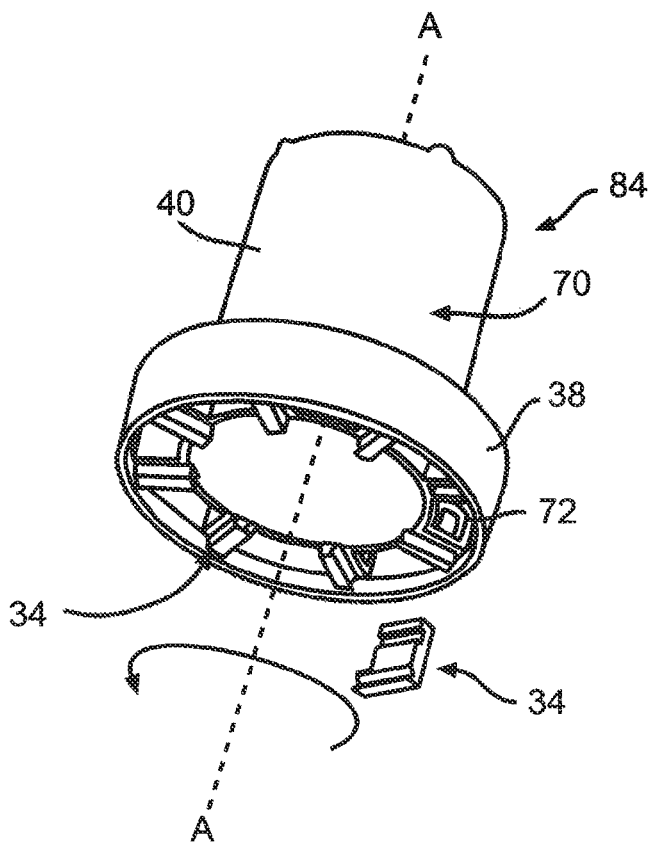
FIG. 8 is a perspective view illustrating an assembly step of the present invention.
Figure 8A:
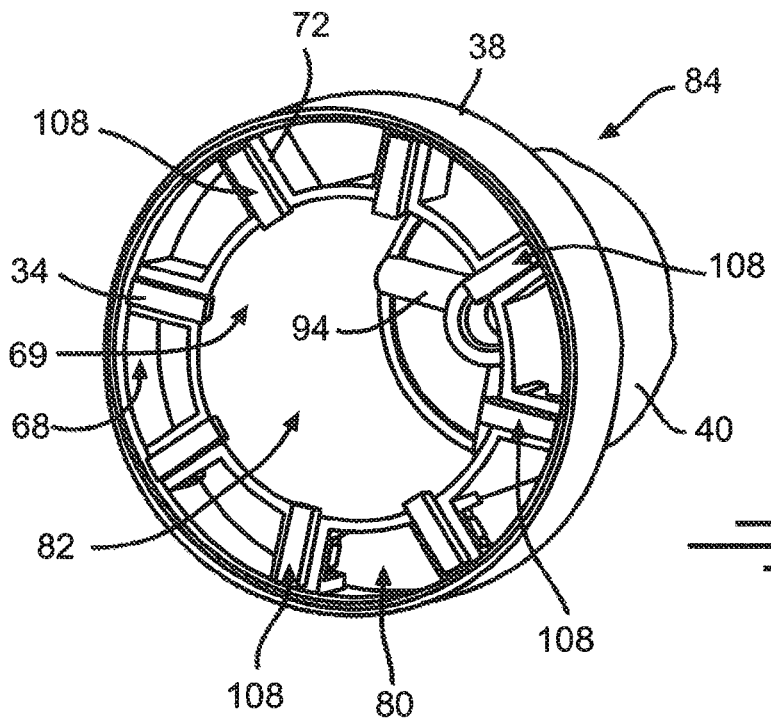
FIG. 8A is a perspective view illustrating a preferred embodiment of an assembled bone cutter assembly of the present invention.

It is preferred that both the first and second cylinders 38, 40 have a hollow interior 80, 82 within their respective inner diameters 42, 48. Such a hollow interior 80, 82 allows for efficient removal of bone debris as the debris can freely flow through the cutter assembly 84 (FIGS. 8, 8A). It is also contemplated that such a housing 32, could be constructed with a cylinder having a solid or partially solid interior.

In a preferred embodiment shown in FIGS. 2, 4, 8A, and 11-11A, the cutter housing 32 has a boss 86 that is positioned within the inner diameter 48 of the second cylinder 40. More specifically, the boss 86 is centrally positioned within the inner diameter 48 of the second cylinder 40. In a preferred embodiment, the boss 86 comprises a throughbore 88. The boss 86 is preferably further positioned within the inner diameter 48 of the second cylinder 40 such that the throughbore 88 is co-axially aligned with the central axis A-A of the housing 32 as shown in FIGS. 2, 4, 8A, and 11-11A.

In a preferred embodiment, illustrated in FIG. 4, the boss 86 is constructed with a distal planar edge 90. This distal planar edge 90 is designed to act as a "stop" to prevent further advancement of the cutter 30 into the end 24 of the bone 14. The boss 86 is preferably positioned with the interior 82 of the second cylinder 40 such that a cut depth 92 is defined between the distal planar edge 90 of the boss 86 and the imaginary second cylinder base plane C-C. It is contemplated that this distal planar edge 90 can be positioned anywhere within the interior 82 of the centrally located second cylinder 40 to establish an optimal cut depth 92 for a particular implant (not shown). In a preferred embodiment the cut depth 92 ranges from about 2 cm to about 10 cm.

A plurality of bars 94 secure the boss 86 within the inner diameter 48 of the centrally located second cylinder 40. A plurality of bars 94, having a length 96 from about 4 cm to about 8 cm and a thickness 98 from about 0.5 cm to about 1 cm, fluidly extend from the interior wall surface 68 of the inner diameter 48 of the first cylinder 38 to the exterior wall surface 70 of the outer diameter 50 of the second cylinder 40 within the proximal portion 64 of the housing 32. It is preferred that a plurality of at least two bars 94, connect the boss 86 within the interior 82 of the second cylinder 40.

It is preferred that the housing 32 be composed of a biocompatible material. In a preferred embodiment, the cutter housing 32 is composed of a biocompatible thermoplastic such as, but not limited to, Acrylonitrile Butadiene Styrene (ABS), Polyarylamide (PAA), or Polyetheretherketone (PEEK).

Furthermore it is preferred that the series of cutter blades 34 are positioned in a radial fashion about the outer diameter 50 of the second cylinder 40 as illustrated in FIGS. 8 and 8A. More specifically, these cutter insert blades 34 are positioned between the exterior surface 70 of the outer diameter 50 of the second cylinder 40 and the interior surface 68 of the inner diameter 42 of the first cylinder 38 at the distal base portion 56 of the housing 32.

Preferred embodiments of the cutter insert blade 34, 130 are shown in FIGS. 5-7. As illustrated, insert blades 34, 130 comprise a blade proximal portion 100 and a blade distal portion 102. The widths 104, 106 of the proximal and distal portions 100, 102 are not necessarily equal. In a preferred embodiment, the width 106 of the distal portion 102 is greater than the width 104 of the proximal portion 100. An insert blade cutting surface 108 preferably extends along the distal width 106 of the insert blade 34, 130. In a preferred embodiment, when inserted into the bone cutter housing 32, the plurality of these blade cutting surfaces 108 align to form an imaginary blade cutting surface plane D-D (FIG. 4). It is further preferred that this imaginary blade cutting surface plane D-D reside between the imaginary first and second cylinder planes B-B, C-C.

As shown in FIGS. 5, 7 and 8A, the distal width 106 of the insert blade 34, 130 is greater than the proximal width 104 of the blade 34, 130. This extra "width portion" of the insert cutter blade 34, 130 is defined as the blade extension portion 110. The blade extension portion 110 is designed such that when the cutter blade 34, 130 is inserted into the housing 32, the extension portion 110 protrudes past the inner diameter 48 of the second cylinder 40 towards the interior 82 of the second cylinder 40.

In addition, the blade extension portion 110 acts as a "free end". This "free end" extension is designed to cut into the head 12 of the bone 14. As such, this "free end" extension 110 defines a new diameter 112 of the bone head 12 as illustrated in FIG. 11A. If such an extension 110 were not present, the interior wall 69 of the second cylinder 40 would prevent cutting of the bone 14. In a preferred embodiment, the blade extension 110 has a width from about 0.05 cm to about 0.10 cm.

As illustrated in FIGS. 5 and 6, a groove 114 is preferably formed within the surface 116 of the distal end portion 102 of the insert blade 34. In a preferred embodiment, the groove 114 has a "V" shape. The groove 114 is designed to establish a rake angle $\theta$ of the insert blade 34. The rake angle $\theta$ is defined as the intersection between the distal surface 120 of the "V" cut out portion 114 and a perpendicular line E-E to the cutting edge surface 108 as shown in FIG. 6. It is preferred that rake angle θ range from about 4° to about 30°.

A relief angle Ø, as illustrated in FIG. 6, is formed between the intersection of the distal end surface 124 of the blade 34 and a tangent line F-F to the blade cutting edge 108. It is preferred that the relief angle Ø range from about 4° to about 20°.

Each cutter blade 34, 130 is preferably positioned within the cutter blade enclosure 72 as shown in FIGS. 8 and 8A. In a preferred embodiment, the insert blade 34, 130 is positioned in the housing 32 such that the proximal end portion 104 of the insert blade 34, 130 resides inside the blade enclosure 72 and the cutting surface 108 of the insert blade 34, 130 lies outside the blade enclosure 72. Furthermore, it is preferred that the cutting surface 108 of the insert blade 34 lies parallel to an imaginary cutting plane D-D as shown in FIG. 4. As shown in FIG. 4, the imaginary cutting plane D-D lies between the first cylinder imaginary plane B-B and the second cylinder imaginary plane C-C. The blade extension 110 preferably is positioned towards the central axis A-A of the assembly 84.

Figure 1:
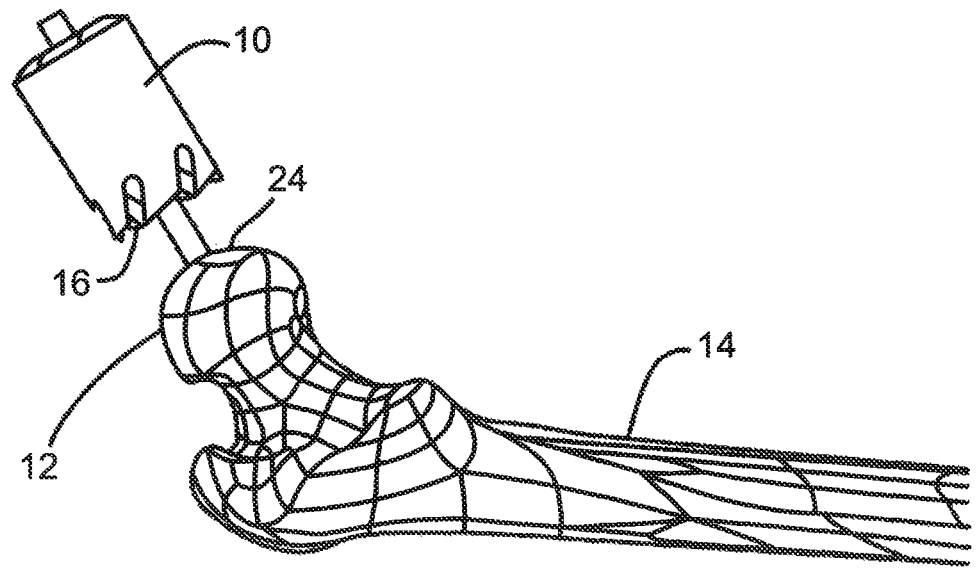
FIG. 1 is a perspective view of a prior art bone cutter and bone.
Figure 1A:
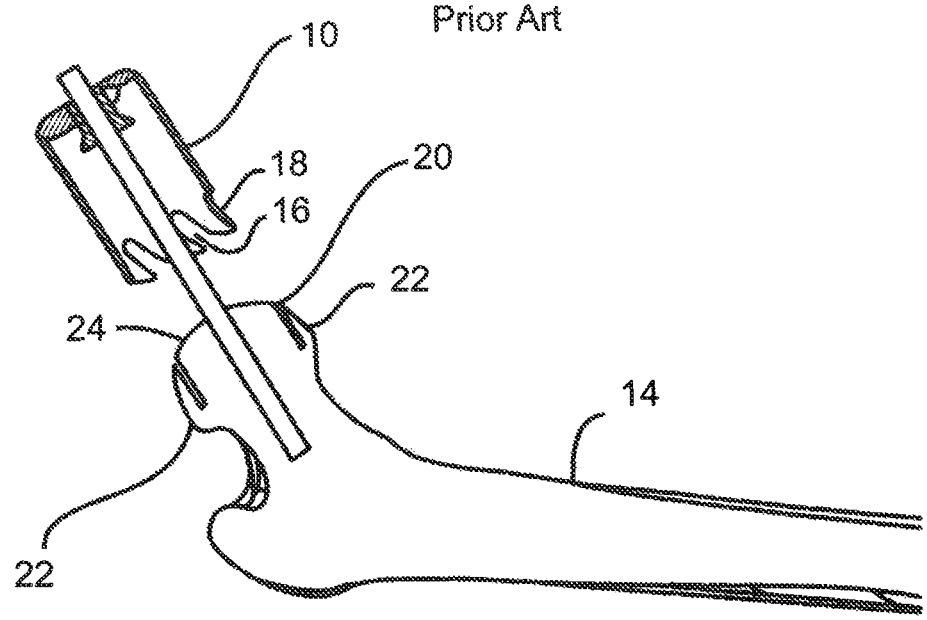
FIG. 1A is a cross-sectional view of the prior art bone cutter and bone shown in FIG. 1.
Figure 2:
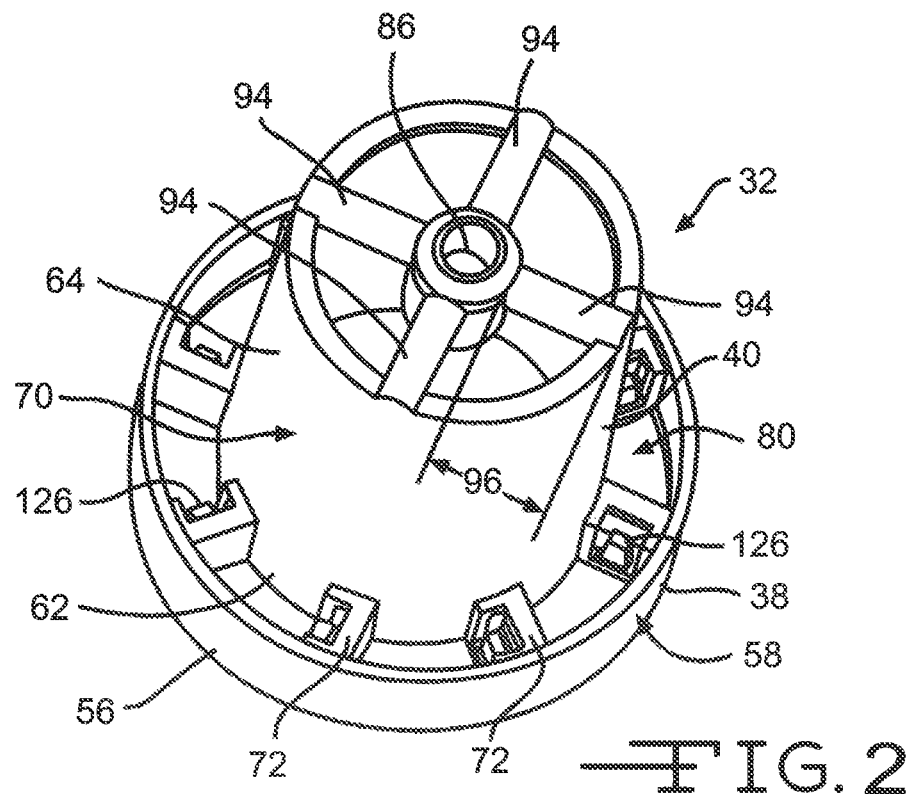
FIG. 2 is a perspective view of the cutter housing of the present invention.
Figure 3:
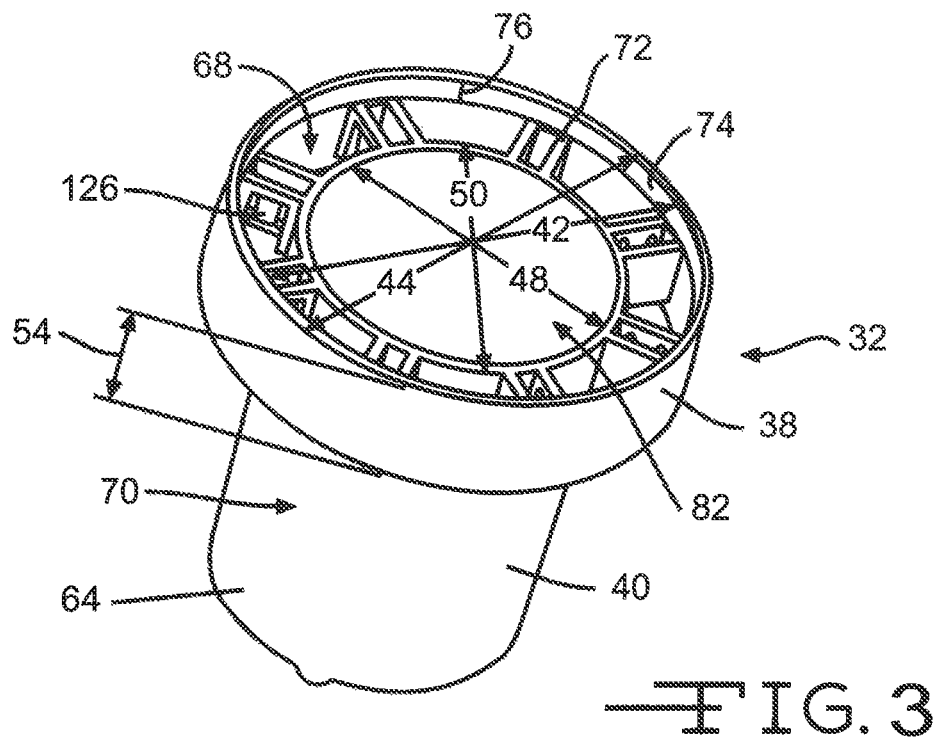
FIG. 3 is an alternate perspective view of the cutter housing of the present invention.

In a preferred embodiment shown in FIGS. 2 and 3, each cutter blade enclosure 72 has a post 126 therewithin. The post 126 is preferably designed to snap-fit into a slot 128 within the proximal end portion 100 of the cutter blade 34 (FIGS. 5 and 6). Once the post 126 snaps into the slot 128, the insert blade 34 is locked within the cutter blade enclosure 72.

In an alternative embodiment, as shown in FIG. 7, the insert blade 130 can be designed without a groove 114 and slot 128. In this embodiment, the cutting edge 108 is formed at the intersection of the side blade surface 116 and the distal end surface 124. It is preferred that a portion of the surface 116 at the proximal end portion 100 of the insert blade 130 has a roughened finish 132. This roughened surface finish portion 132 provides for a more secure fit when positioned within the blade enclosure 72.

In a preferred embodiment, insert blades 34, 130 are secured within the blade enclosure 72 with an induction bonding process. Alternatively, the insert blade 34, 130 can be secured by an alternate means not limited to adhesives, overmolding, press fitting, induction bonding, and the like.

Figure 10A:
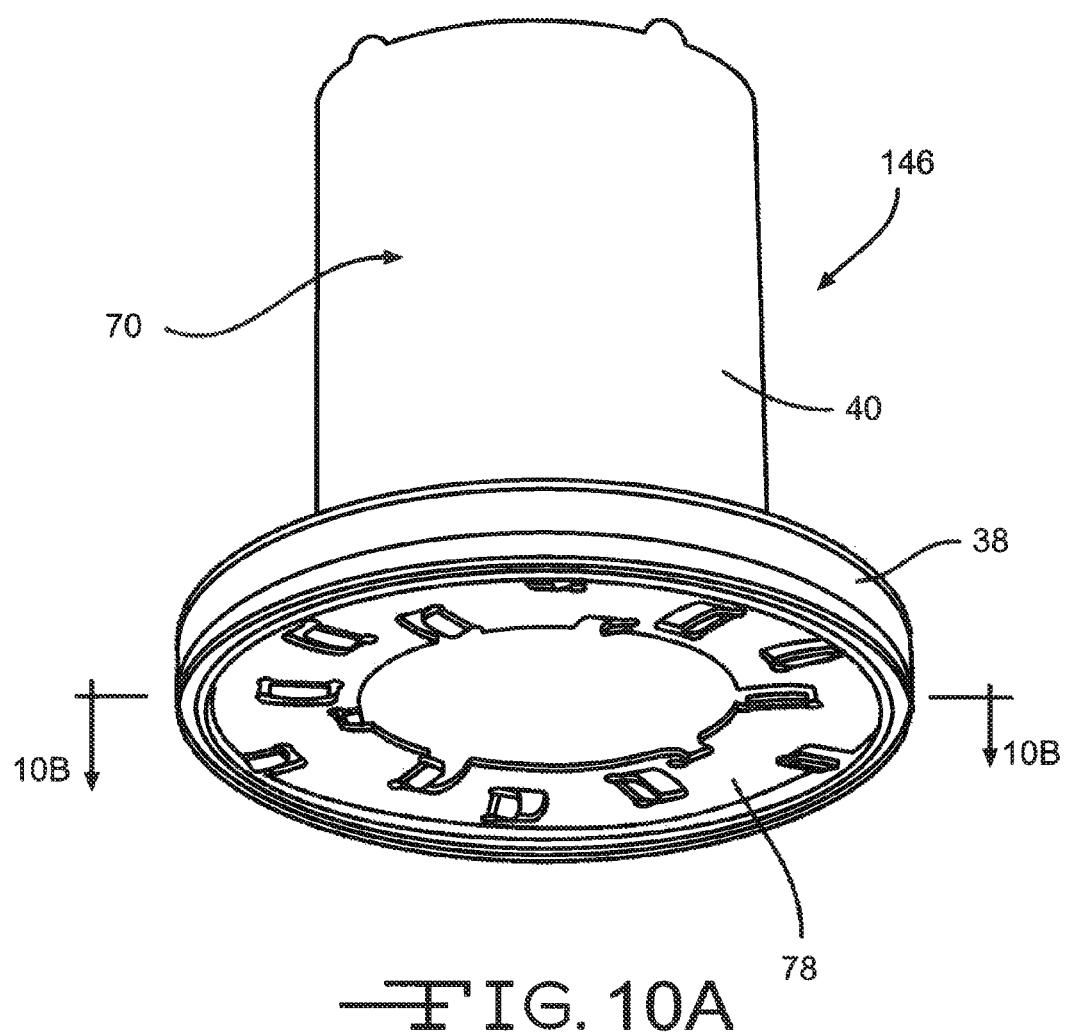
FIG. 10A is a perspective view of an assembled alternate embodiment of the bone cutter assembly of the present invention shown in FIG. 10.

In an alternate embodiment, the cutting disc 78 is positioned at the distal end portion 67 of the housing 32. The cutting disc 78 embodiment provides an additional means of bone removal which is illustrated in FIGS. 9-10A. An embodiment of this alternate cutter assembly 146 is shown in FIG. 10A. The assembly 146 of this embodiment comprises the housing 32 and the cutter disc 78.

Figure 10B:
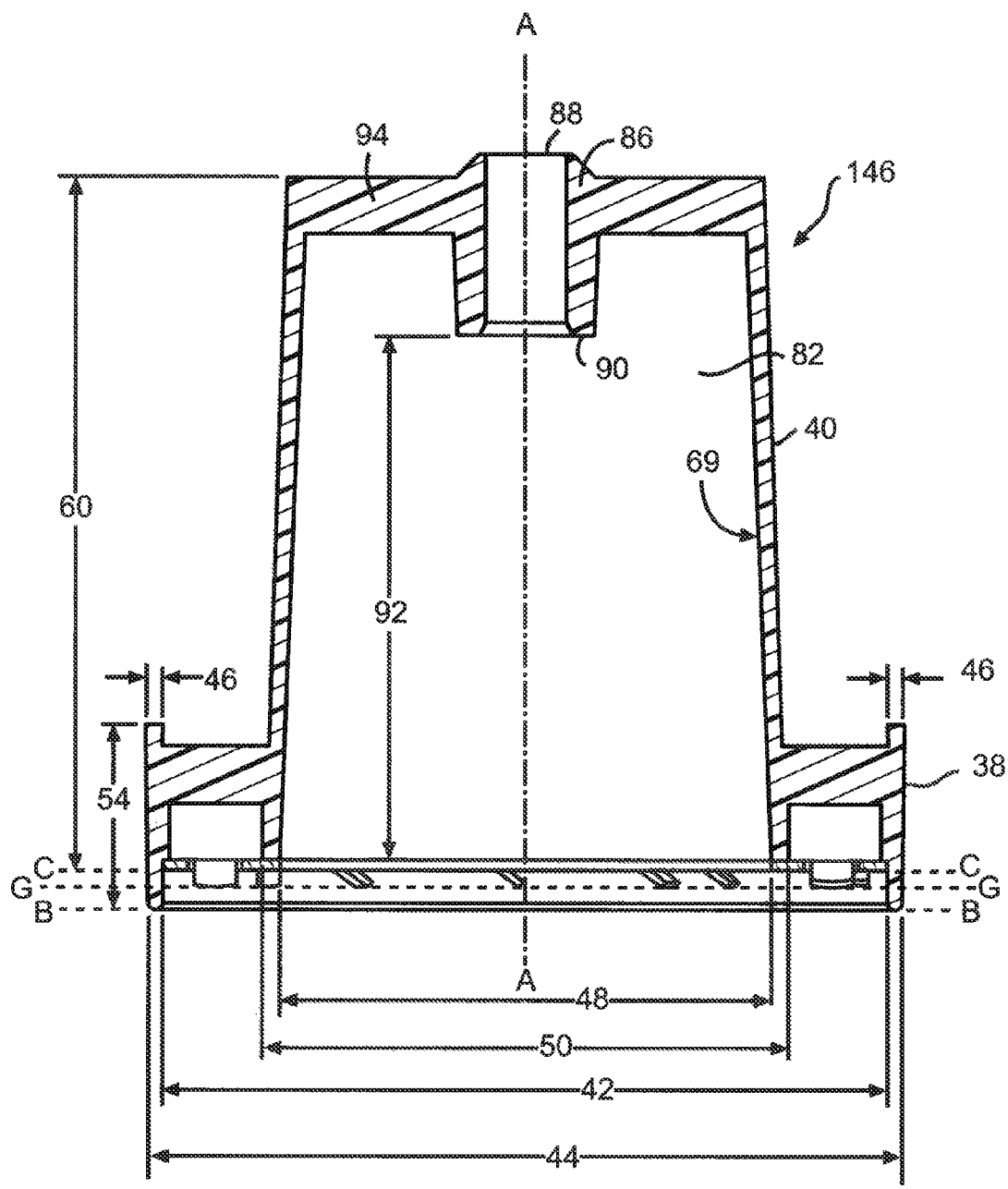
FIG. 10B is a cross-sectional view of an assembled alternate embodiment of the bone cutter assembly of the present invention shown in FIG. 10.

The cutting disc 78 preferably comprises an outer disc diameter 134, an inner disc diameter 136 and a planar surface 138 therebetween. The cutting disc 78 is positioned between the wall thickness 46 of the first cylinder 38 and the wall thickness 52 of the second cylinder 40 at the distal end portion 67. More specifically, it is preferred that the cutting disc 78 be placed between the inner diameter 42 of the first cylinder 38 and the inner diameter 48 of the second cylinder 40 such that the planar surface 138 of the cutting disc 78 is parallel to the first and second cylinder imaginary planes B-B, C-C (FIG. 10B).

Positioned throughout the surface 138 of the disc 78 are a series of openings 140. These openings 140 are preferably positioned throughout the surface 138 of the disc 78 in a helical pattern. Protruding from the opening 140 is a cutting tooth 142. The cutting teeth 142 are designed such that a cutting surface 144 is positioned outwardly from the planar surface 138 of the disc 78. Alternately, the cutting surface 144 may protrude inwardly from the surface 138 of the disc 78. In a preferred embodiment, these cutting surfaces 144 of the cutting teeth 142 align to form an imaginary cutting disc plane G-G. This imaginary plane G-G preferably resides between the first and second imaginary cylinder planes B-B, C-C (FIG. 10B).

It is preferred that the cutter insert blades 34, 130 and the cutting disc 78 are composed of a biocompatible metal. In a preferred embodiment, such biocompatible metals include, but are not limited to, stainless steel, MP35N, titanium, and combinations thereof. It is most preferred that cutter blades 34, 130 and the cutting disc 78 are composed of a 300 series stainless steel.

In a preferred embodiment, the cutter housing 32 is first molded from a biocompatible polymer as previously mentioned. After the housing 32 has been molded, the cutter blades 34, 130 or cutter disc 78 are then inserted in the distal base portion 67 of the housing 32. As previously mentioned, an induction bonding process is preferably used to secure the cutter blades 34, 130 or cutter disc 78 to the molded assembly 84, 146. Alternatively, adhesives, overmolding, press fitting, and the like may also be used.

In this preferred bonding embodiment, electromagnetic current is used to heat the blades 34, 130 or blade disc 78. Heat generated from the current, melts the surrounding assembly polymer material, causing the material to flow and engage the cutter blades 34, 130 or disc 78. It is well known that alternative processes such as cross pinned engagements, direct insert molding, or ultrasonic insertion may also be used to strengthen the connection or act as a primary means to join the bone cutter 30 of the present invention.

FIGS. 11 and 11A illustrate the use of the bone cutter 30 of the present invention. Initially, a guide-hole 148 is drilled into the end 24 of a bone 14. The guide rod 36 is placed into the guide-hole 148 and the cutter assembly 84, 146 is placed over the rod 36 as shown. In a preferred embodiment, the guide rod 36 is preferably positioned through the central axis A-A of the bone cutter 30.

Once in place over the end 24 of the bone 14, the cutter 30 is rotated in either a clockwise or counterclockwise direction. This rotational movement of the cutter 30, removes bone material from the end 24 of the bone 14 with a smooth surface finish with a bone diameter 112 suitably sized for insertion of an implant (not shown). Once the bone head 12 is properly shaped, the cutter 30 and guide rod 36 are removed. An implant (not shown) is then positioned over the end 24 of the bone 14.

Now, it is therefore apparent that the present invention has many features and benefits among which are promoting proper implant fit, decreased procedural times and minimized patient trauma. While embodiments of the present invention have been described in detail, that is for the purpose of illustration, not limitation.

What is claimed is:
1. A bone cutter, comprising:
 a) a first sidewall comprising a first inner surface providing a first lumen extending along a longitudinal axis from a first sidewall proximal portion to a first sidewall distal portion having a first sidewall distal end residing along a first imaginary plane;
 b) a second sidewall comprising a second inner surface spaced from a second outer surface by a second sidewall thickness to thereby provide a second lumen extending along the longitudinal axis from a second sidewall proximal portion to a second sidewall distal Portion having a second sidewall distal end residing along a second imaginary plane, c) wherein the first and second sidewalls are fixedly joined to each other in a co-axial relationship with the outer surface of the second sidewall being radially inside the inner surface of the first sidewall with the second imaginary plane being more proximal along the longitudinal axis than the first imaginary plane to thereby provide an offset;

d) a cutter disc comprising a disc wall extending from an annular outer disc edge to an inner disc edge surrounding a disc opening, the cutter disc having a disc thickness extending from a proximal disc face to a distal disc face, wherein the proximal cutter disc face is supported on the second sidewall distal end with the annular outer disc edge in contact with the inner surface of the first sidewall distal portion; and e) a plurality of cutting teeth on the cutter disc, each cutting tooth having a tooth opening extending through the disc wall and a tooth cutting surface extending away from the distal disc face towards the first imaginary plane, wherein each tooth opening provides open communication at least into the first lumen between the first and second sidewalls.

2. The bone cutter of claim 1 wherein an inner diameter of the second sidewall is greater than an inner diameter at the inner disc edge of the cutter disc.

3. The bone cutter of claim 1 wherein a distal end of each of the tooth cutting surfaces is co-planar with an imaginary disc cutting plane.

4. The bone cutter of claim 3 wherein the imaginary disc cutting plane is positioned between the first imaginary plane and the second imaginary plane.

5. The bone cutter of claim 1 wherein a second height of the second sidewall measured from a second sidewall proximal end to the second sidewall distal end is greater than a first height of the first sidewall measured from a first sidewall proximal end to the first sidewall distal end.

6. The bone cutter of claim 1 wherein a plurality of spaced apart connectors are positioned radially between the inner surface of the first sidewall and the outer surface of the second sidewall to thereby connect the first sidewall to the second sidewall.

7. The bone cutter of claim 1 wherein a boss at the second sidewall proximal portion has a throughbore that is co-axial with the longitudinal axis.

8. The hone cutter of claim 1 wherein the cutter disc is composed of a biocompatible metal.

9. The bone cutter of claim 1 wherein the outer annular disc edge contacts an offset rim at the first inner surface of the first sidewall.

10. The bone cutter of claim 1 wherein the cutter disc supported on the second sidewall distal end is removable therefrom for replacement of the cutter disc.

11. A bone cutter, comprising:

a) a first sidewall comprising a first inner surface providing a first lumen extending along a longitudinal axis from a first sidewall proximal portion to a first sidewall distal portion having a first sidewall distal end residing along a first imaginary plane;

b) a second sidewall comprising a second inner surface spaced from a second outer surface by a second thickness to thereby provide a second lumen extending along the longitudinal axis from a second sidewall proximal portion to a second sidewall distal portion having a second sidewall distal end residing along a second imaginary plane, c) wherein the first and second sidewalls are fixedly joined to each other in a co-axial relationship with the outer surface of the second sidewall being radially inside the inner surface of the first sidewall with the second imaginary plane being more proximal along the longitudinal, axis than the first imaginary plane to thereby provide an offset;

d) a cutter disc comprising a disc wall extending from an annular outer disc edge to an outer annular inner disc edge surrounding a disc opening, the cutter disc having a disc thickness extending from a proximal disc face to a planar distal disc face, wherein the proximal cutter disc face is supported on the second sidewall distal end with the annular outer disc edge contacting the inner surface of the first sidewall distal portion; and e) a plurality of cutting teeth, each cutting tooth having a tooth opening extending through the disc wall and a tooth cutting surface extending distally away from the planar distal disc face and towards the first imaginary base plane, and wherein a distal end of each tooth cutting surface is co-planar with an imaginary disc cutting plane fixedly positioned between the first and second cylinder imaginary base planes, wherein each tooth opening provides open communication at least into the first lumen between the first and second sidewalls.

12. The bone cutter of claim 11 wherein an inner diameter of the second sidewall is greater than an inner diameter at the inner disc edge of the cutter disc.

13. The bone cutter of claim 11 wherein a boss at the second sidewall proximal portion has a throughbore that is co-axial with the longitudinal axis.

14. The bone cutter of claim 11 wherein a plurality of spaced apart connectors are positioned radially between the inner surface of the first sidewall and the outer surface of the second sidewall to thereby connect the first sidewall to the second sidewall.

15. The bone cutter of claim 11 wherein the outer annular disc edge contacts an offset rim at the first inner surface of the first sidewall.

16. The bone cutter of claim 11 wherein the cutter disc supported on the second sidewall distal end is removable therefrom for replacement of the cutter disc.

17. A bone cutter, comprising:

a) a first sidewall comprising a first inner surface providing a first lumen extending along a longitudinal axis from a first sidewall proximal portion to a first sidewall distal portion having a first sidewall distal end residing along a first imaginary plane;

b) a second sidewall comprising a second inner surface spaced from a second outer surface by a second sidewall thickness to thereby provide a second lumen extending along the longitudinal axis from a second sidewall proximal portion to a second sidewall distal portion having a second sidewall distal end residing along a second imaginary plane, c) wherein the first and second sidewalls are fixedly joined to each other in a co-axial relationship by a plurality of spaced apart connectors positioned radially between the inner surface of the first sidewall and the outer surface of the second sidewall with the second imaginary plane being more proximal along the longitudinal axis than the first imaginary plane to thereby provide an offset;

d) a boss at the second sidewall proximal portion having a throughbore that is co-axial with the longitudinal axis;

e) a cutter disc comprising a disc wall extending from an outer disc edge to an inner disc edge surrounding a disc opening, the cutter disc having a disc thickness extending from a proximal disc face to a distal disc face, wherein the proximal cutter disc face is supported on the second sidewall distal end with the annular outer disc edge in contact with the inner surface of the first sidewall distal portion; and f) a plurality of cutting teeth on the cutter disc, each cutting tooth having a tooth opening extending through the disc wall and a tooth cutting surface extending away from the distal disc face towards the first imaginary plane, wherein the plurality of tooth cutting surfaces reside along a third imaginary plane that is between the first and second imaginary planes of the respective first and second sidewall distal ends, and wherein each tooth opening provides open communication into the first and second lumens of the respective first and second sidewalls.

18. The bone cutter of claim 17 wherein an inner diameter of the second sidewall is greater than an inner diameter at the inner disc edge of the cutter disc.

* * * * *

UNITED STATES PATENT AND TRADEMARK OFFICE
CERTIFICATE OF CORRECTION

PATENT NO. : 8,876,825 B2  
APPLICATION NO. : 13/112084  
DATED : September 9, 2014  
INVENTOR(S) : Gary C. Victor Page 1 of 1

It is certified that error appears in the above-identified patent and that said Letters Patent is hereby corrected as shown below:

In the Claims

Column 8, line 65 (Claim 1, line 11) delete "Portion" and insert --portion--

Column 10, line 3 (Claim 11, line 18) after the word "longitudinal" delete the ","

Column 10, line 7 (Claim 11, line 22) before the words "inner disc" delete the words "outer annular"

Signed and Sealed this  
Tenth Day of March, 2015

Michelle K. Lee  
*Deputy Director of the United States Patent and Trademark Office*